(12) United States Patent
Yang

(10) Patent No.: US 7,781,075 B2
(45) Date of Patent: Aug. 24, 2010

(54) ORGANIC LIGHT-EMITTING MATERIAL AND ORGANIC LIGHT-EMITTING DEVICE

(75) Inventor: Chun-Hui Yang, Fuli Township, Hualien County (TW)

(73) Assignee: Au Optronics Corporation, Science-Based Industrial Park, Hsin-Chu (TW)

( * ) Notice: Subject to any disclaimer, the term of this patent is extended or adjusted under 35 U.S.C. 154(b) by 1127 days.

(21) Appl. No.: 11/409,934

(22) Filed: Apr. 24, 2006

(65) Prior Publication Data

US 2007/0054150 A1    Mar. 8, 2007

(30) Foreign Application Priority Data

Sep. 7, 2005    (TW)    .............................. 94130745 A

(51) Int. Cl.
  *H01L 51/54*    (2006.01)
  *C09K 11/06*    (2006.01)
(52) U.S. Cl. .................. 428/690; 428/917; 313/504; 313/506; 257/E51.044; 546/4; 548/101
(58) Field of Classification Search .................. None
  See application file for complete search history.

(56) References Cited

U.S. PATENT DOCUMENTS

| 6,858,327 | B2 | 2/2005 | Tsai et al. | |
|---|---|---|---|---|
| 7,507,486 | B2 * | 3/2009 | Ren | .................. 428/690 |
| 2001/0015432 | A1 | 8/2001 | Igarashi | |
| 2002/0134984 | A1 | 9/2002 | Igarashi | |
| 2003/0197183 | A1 | 10/2003 | Grushin et al. | |
| 2004/0086743 | A1 | 5/2004 | Brown et al. | |
| 2004/0102632 | A1 | 5/2004 | Thompson et al. | |

OTHER PUBLICATIONS

J.W.A.M. Janssen, H.J. Koeners, C.G. Kruse, and C.L. Habraken; "The Preparation of 3(5)-Nitropyrazoles by Thermal Rearrangement of N-Nitropyrazoles;" May 1973; pp. 1777-1782, J. Org. Chem., 38(10).

J.W.A.M. Janssen, c.L. Habraken; "Rearrangment of N-Nitropyrazoles. The Formation of Nitropyrazoles;" pp. 3081-3084, J. Org. Chem., 36(21), 1971.

* cited by examiner

*Primary Examiner*—Marie R. Yamnitzky
(74) *Attorney, Agent, or Firm*—Thomas, Kayden, Horstemeyer & Risley, LLP

(57) ABSTRACT

An organic light-emitting device is provided, which comprises an anode, a cathode and a light-emitting layer between them. An organic light-emitting material having the structure of Formulas I or II is doped in the light-emitting layer. In the Formulas I and II, $R_1$~$R_9$ are H, F, $CF_3$, $NO_2$, an alkyl group of 1 to 6 carbon atoms, an aryl group or any combinations thereof; and M is a transition metal atom.

15 Claims, 1 Drawing Sheet

ORGANIC LIGHT-EMITTING MATERIAL AND ORGANIC LIGHT-EMITTING DEVICE

RELATED APPLICATIONS

The present application is based on, and claims priority from, Taiwan Application Serial Number 94130745, filed Sep. 7, 2005, the disclosure of which is hereby incorporated by reference herein in its entirety.

BACKGROUND

1. Field of Invention

The present invention relates to a light-emitting material and a light-emitting device. More particularly, the present invention relates to a new organic light-emitting material and a new organic light-emitting device.

2. Description of Related Art

In 1996, Pioneer of Japan announced the first green display of 256×64 pixels, which was the first time that an organic light-emitting diode (OLED) was applied to a flat panel display. Since that time, there have been great improvements in organic light-emitting displays. Organic light-emitting displays are lightweight, thin, low in cost, power efficient, self-emitting, easy to manufacture and have large viewing angle and fast response time. Because of these advantages, organic light-emitting diodes show great potential in display products and are expected to be the next-generation flat panel displays and light sources.

The current trend of organic light-emitting displays is toward full-color displays. Although organic light-emitting materials of red, blue and green, the three colors that traditional full-color displays required, have been discovered and developed successfully, their quality and performance are not optimum. Markets need organic light-emitting materials with better quality and performance, especially organic light-emitting materials of blue and red color. Moreover, organic light-emitting diodes providing white light, which is often used as ambient light, are also in great demand.

The ligands of metal complexes, which are doped in a light-emitting layer of a traditional organic light-emitting diode, are mostly conjugate rings of six-six member rings, six-five member rings or even larger rings. Because the ligands have larger conjugate rings, the light-emitting of these type organic light-emitting diodes probably located at orange to red area and the wavelength range that can be adjusted is narrower. Traditional organic light-emitting diodes mainly emit red light.

SUMMARY

It is therefore an aspect of the present invention to provide an organic light-emitting material, which uses five-five member rings to be the ligands of a transition metal complex. Because the conjugate ring of the ligands of the organic light-emitting material is smaller than that of a traditional organic light-emitting material, the light-emitting wavelength of the organic light-emitting material is more blue shift than that of the traditional light-emitting material. Moreover, the organic light-emitting material has a broader wavelength range to be adjusted. The light-emitting color can be altered by changing substituents of the five-five member rings of the ligands of the transition metal complex of the organic light-emitting material.

Another aspect of the present invention is to provide an organic light-emitting material, which can provide the red, blue and green colors needed by traditional full color displays and white light organic light-emitting devices. The light-emitting quality of the organic light-emitting material is good and its luminescence efficiency is high.

Another aspect of the present invention is to provide a manufacturing method of an organic light-emitting material, whose yield rate is high when synthesizing a transition metal complex having ligands of five-five member rings.

Still another aspect of the present invention is to provide an organic light-emitting device, which has high luminescence efficiency of about 4 cd/A to about 10 cd/A.

In accordance with the foregoing and other aspects, one embodiment of the present invention provides an organic light-emitting material having the structure of Formulas I or II,

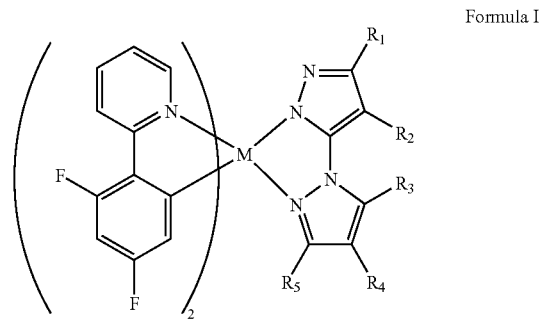

Formula I

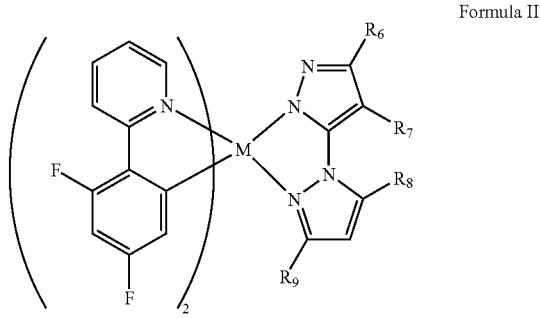

Formula II wherein each of $R_1$-$R_9$ is independently H, F, $CF_3$, an alkyl group of 1 to 6 carbon atoms, or an aryl group; and M is a transition metal atom.

In accordance with the foregoing and other aspects, one embodiment of the present invention provides a manufacturing method of the organic light-emitting material, which comprises reacting a compound of Formula III with a compound of Formulas IV or V and a base compound in a solvent,

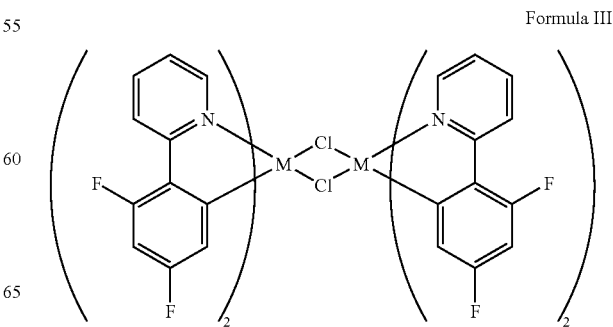

Formula III

-continued

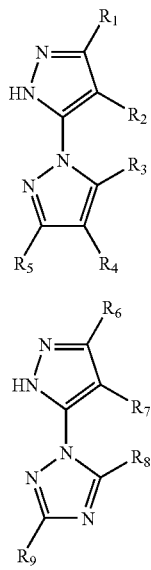

Formula IV

Formula V wherein each of $R_1$-$R_9$ is independently H, F, $CF_3$, an alkyl group of 1 to 6 carbon atoms, or an aryl group; and M is a transition metal atom.

In accordance with the foregoing and other aspects, one embodiment of the present invention provides an organic light-emitting device, which comprises an anode, a cathode and a light-emitting layer. The light-emitting layer is between the anode and the cathode and contains an organic light-emitting material having the structure of Formulas I or II,

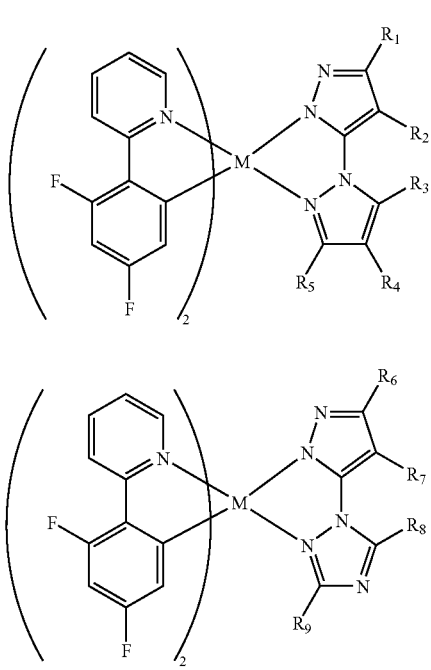

Formula I

Formula II wherein each of $R_1$-$R_9$ is independently H, F, $CF_3$, an alkyl group of 1 to 6 carbon atoms, or an aryl group; and M is a transition metal atom. The doping concentration of the organic light-emitting material in the light-emitting layer is about 5% to 20%.

In conclusion, the invention provides a method to synthesize the transition metal complex having ligands of five-five member rings. Using the transition metal complex to dope the light-emitting layer of the organic light-emitting device, the organic light-emitting device can have not only a broadly adjustable light-emitting wavelength range but also high luminescence efficiency.

BRIEF DESCRIPTION OF THE DRAWINGS

The accompanying drawings are included to provide a further understanding of the invention, and are incorporated in and constitute a part of this specification. The drawings illustrate embodiments of the invention and, together with the description, serve to explain the principles of the invention. In the drawings.

DETAILED DESCRIPTION OF THE PREFERRED EMBODIMENTS

Organic Light-Emitting Material

Figure 1:
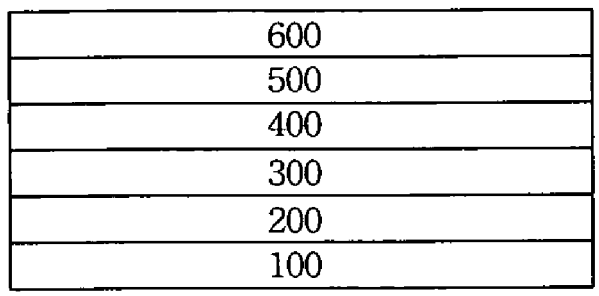
FIG. 1 is the structure of the organic light-emitting device according to one preferred embodiment of this invention.

Organic light-emitting material provided herein have the structure of Formulas I or II,

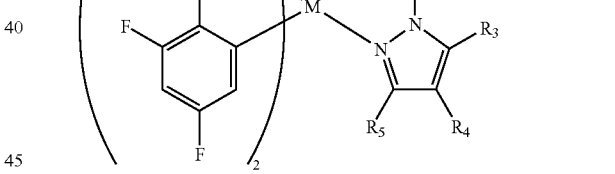

Formula I

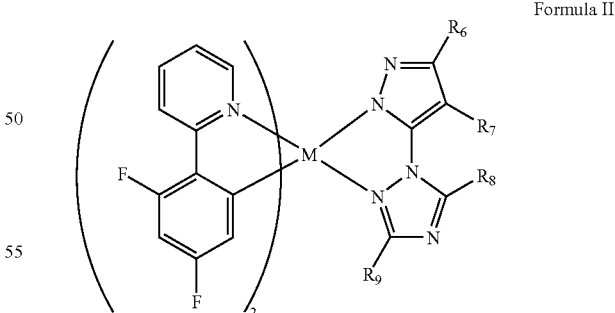

Formula II wherein each of $R_1$-$R_9$ is independently H, F, $CF_3$, an alkyl group of 1 to 6 carbon atoms, or an aryl group; and M is a transition metal atom. In a preferred embodiment, the transition metal is Ir, Ru, Rh, Pd, Os or Pt, most preferably Ir.

Compounds B-F listed hereinafter are examples of the organic light-emitting material of the preferred embodiment of the invention which may illustrate the concept of the invention.

Compound A

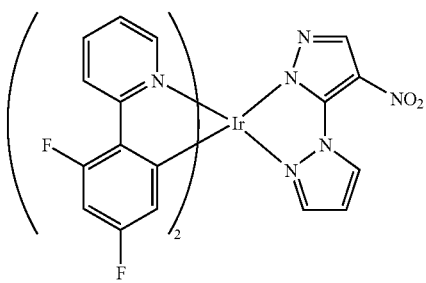

No phosphorescence

Compound B

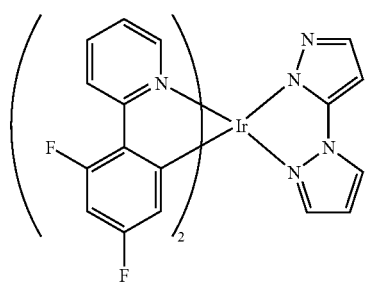

492 nm

Compound C

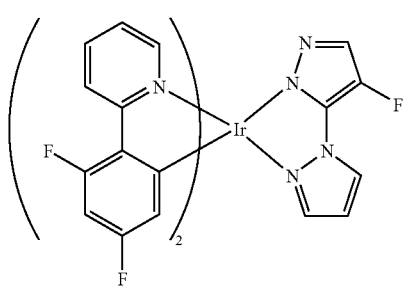

512 nm

Compound D

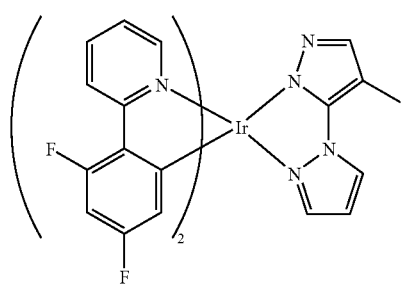

536 nm

Compound E

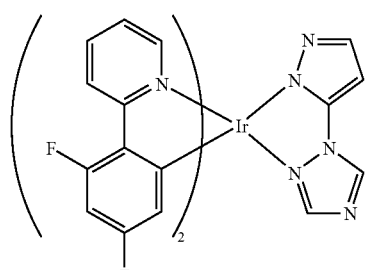

480 nm, 500 nm

-continued

Compound F

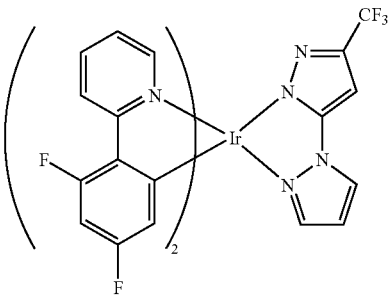

474 nm, 498 nm

Compounds B-D and Compound F have the structure of Formula I, and Compound E has the structure of Formula II. Except for Compound A, which has no phosphorescence, the light-emitting wavelength range of the other compounds is about 450 nm to about 550 nm.

The compounds in order of increasing wavelength from short to long are Compound F, Compound E, Compound B, Compound C and Compound D. Among these compounds, both Compound F and Compound E have two main light-emitting wavelengths so the wavelength range they cover is broader. The light-emitting wavelength of Compound B is 492 nm so it can be the material of a blue light-emitting layer. The light-emitting wavelength of Compound C is 512 nm so it can be the material of a green light-emitting layer. The light-emitting wavelength of Compound D is 536 nm so it can be the material of a yellow light-emitting layer. Moreover, the full-width half-maximum (FWHM) of the peak in the spectrum of Compound D is quite broad, which makes Compound D suitable to be a white light organic light-emitting device.

Manufacturing Method of the Organic Light-Emitting Material

The organic light-emitting material of Formula I is produced by reacting a compound of Formula III with a compound of Formula IV and a base compound in a solvent.

The organic light-emitting material of Formula II is produced by reacting a compound of Formula III with a compound of Formula V and a base compound in a solvent.

The above reaction is reacted under a thermal reflux environment. The base compound used in the reaction is preferably sodium ethoxide (NaOEt), potassium hydroxide, or sodium hydroxide. The solvent is preferably ethylene glycol monoethyl ether.

The structures of Formula III, Formula IV and Formula V are:

Formula III

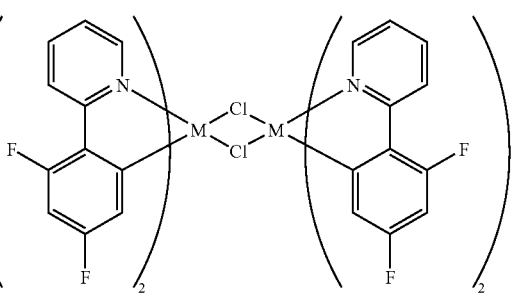

Formula IV

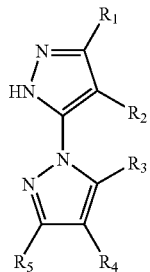

Formula V

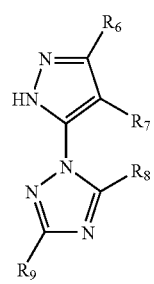

wherein each of $R_1$-$R_9$ is independently H, F, $CF_3$, an alkyl group of 1 to 6 carbon atoms, or an aryl group; and M is a transition metal atom. In a preferred embodiment, the transition metal is Ir, Ru, Rh, Pd, Os or Pt, most preferably Ir.

The synthetic reaction equation of the organic light-emitting material of Formula I is:

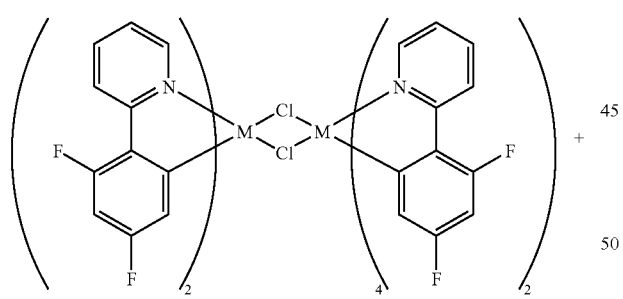

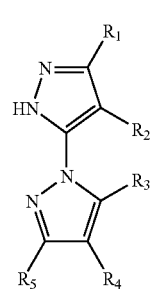

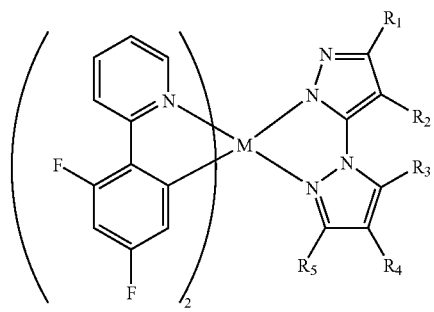

The synthetic reaction equation of the organic light-emitting material of Formula II is:

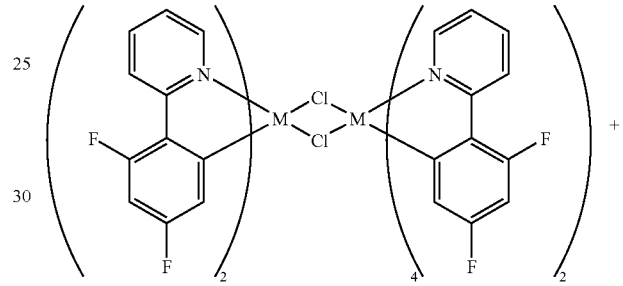

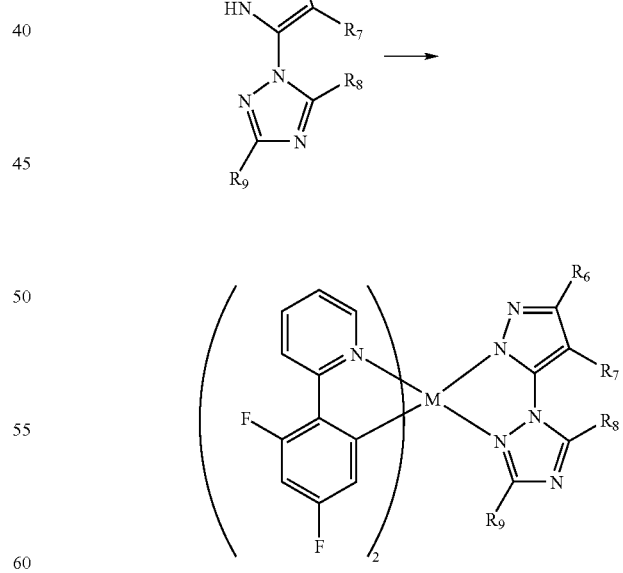

Compounds B'-D' and Compound F' are preferred examples of Formula IV. Compound E' is a preferred example of Formula V. The chemical structures of the compounds are portrayed as:

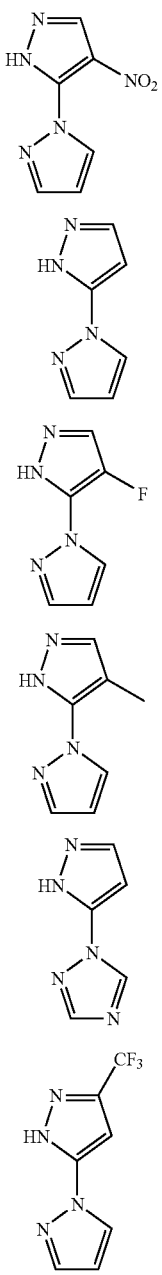

Compound A'

Compound B'

Compound C'

Compound D'

Compound E'

Compound F'

In the embodiment, the organic light-emitting material of Formula I was produced by reacting 1 equivalent of a Formula IV compound (Compounds B'-D' and Compound F') with 0.5 equivalent of a Formula III compound and 0.5 equivalent of sodium ethoxide dissolved in ethylene glycol monoethyl ether. The reaction was reacted under a thermal reflux environment for 16 hours. Then, deionized water and dichloromethane were used to extract the product several times. Then, dichloromethane and hexane were used as solvents to recrystallize the product. Finally, the organic light-emitting material of Formula I (Compounds B-D and Compound F) were obtained. The yield rate was about 50%.

In the embodiment, the organic light-emitting material of Formula II was produced by reacting 1 equivalent of Compound E' of Formula V with 0.5 equivalent of a Formula III compound and 0.5 equivalent of sodium ethoxide dissolved in ethylene glycol monoethyl ether. The reaction was reacted under a thermal reflux environment for 16 hours. Then, deionized water and dichloromethane were used to extract the product several times. Then, dichloromethane and hexane were used as solvents to recrystalize the product. Finally, the organic light-emitting material of Compound E of Formula II was obtained. The yield rate was about 50%.

The following is the synthesis reaction equation of Compounds A'~F'. More detailed synthetic methods can be found by C. L. Habraken, J. Org. Chem., 38, 10, 1973, 1777 or J. W. A. M. Janssen, and C. L. Habraken, J. Org. Chem., 36, 21, 1971, 3081.

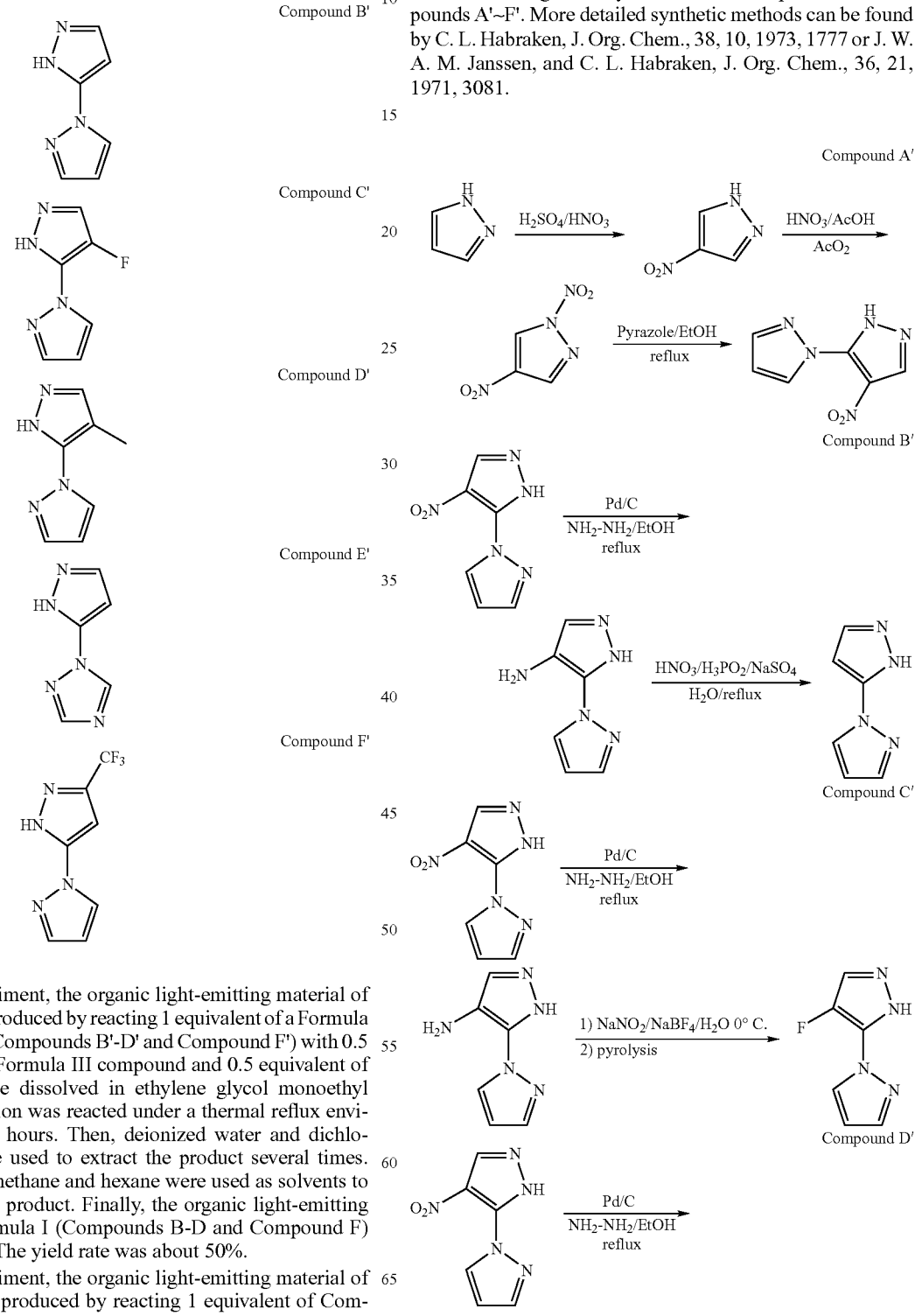

-continued

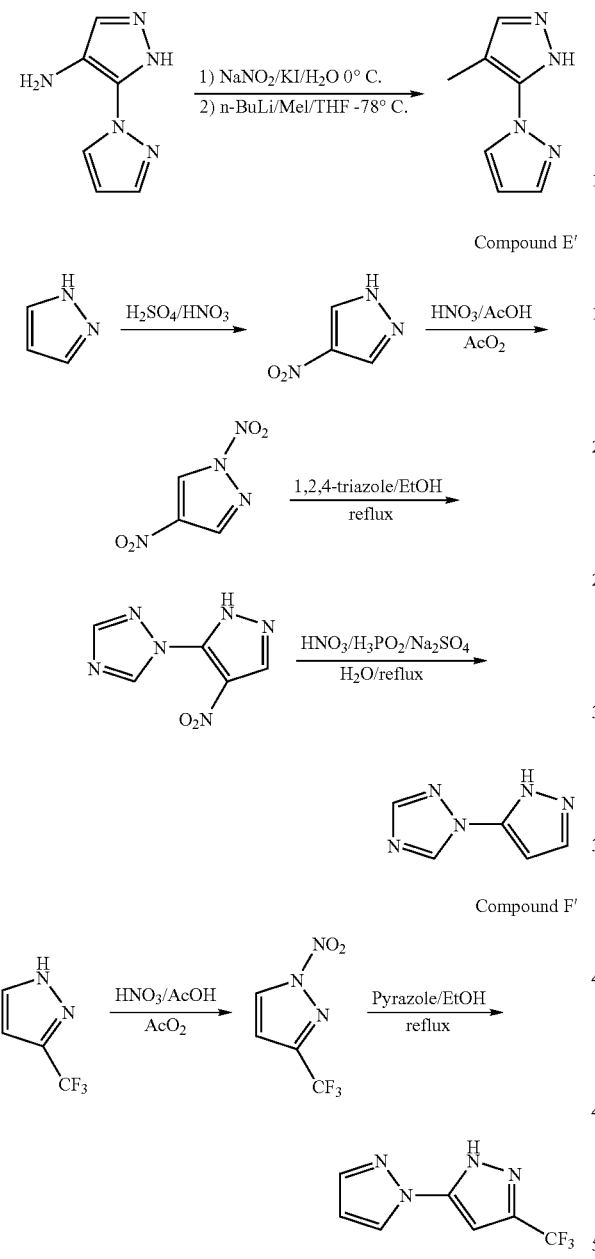

Organic Light-Emitting Device

The organic light-emitting device comprises an anode, a cathode and a light-emitting layer. Moreover, the organic light-emitting device can further comprise a hole injecting layer, a hole transporting layer, an electron transporting layer. These layers are oriented in the order of the anode, the hole injecting layer, the hole transporting layer, the light-emitting layer, the electron transporting layer and the cathode. The organic light-emitting material of Formulas I or II is doped in the light-emitting layer of the organic light-emitting device. The doping concentration of the Formulas I or II organic material in the light-emitting layer is about 5% to about 20%.

The light-emitting wavelength of the organic light-emitting device is close to that of the organic light-emitting material. The light-emitting wavelength range of the organic light-emitting device is about 450 nm to about 550 nm. The luminescence efficiency of the organic light-emitting device is about 4 cd/A to about 10 cd/A.

Figure 2:
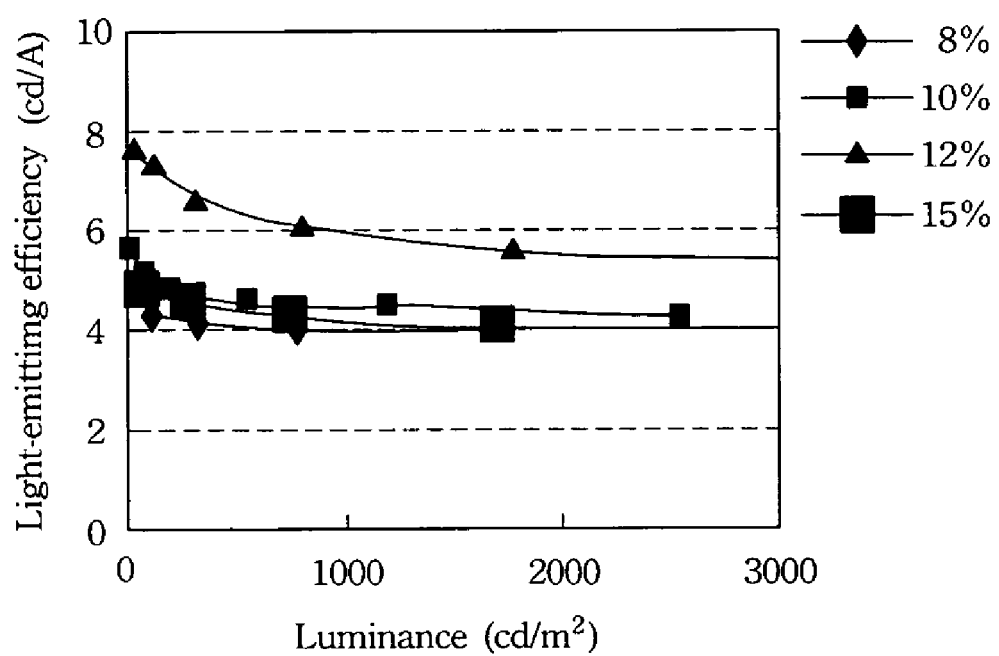
FIG. 2 is the luminescence efficiency of the organic light-emitting device according to one preferred embodiment of this invention.

FIG. 1 is the structure of the organic light-emitting device according to one preferred embodiment of this invention. In FIG. 1, the layer structure of the organic light-emitting device is ordered as the anode 100, the electrical hole injecting layer 200, the electrical hole transporting layer 300, the light-emitting layer 400, the electron transporting layer 500 and the cathode 600. The anode 100 is indium tin oxide (ITO). The cathode 600 is aluminum. Moreover, the light-emitting layer 400 of the organic light-emitting device is doped with the organic light-emitting material of Compound B. Different doping concentrations were used to test their influence on the light-emitting properties of the organic light-emitting device. FIG. 2 is the test result.

In FIG. 2, when the doping concentration of Compound B in the light-emitting layer is 12%, the organic light-emitting device has the best luminescence efficiency of 8 cd/A. Higher or lower doping concentrations produce poorer luminescence efficiency. Moreover, the light-emitting wavelength of the organic light-emitting device changes with the doping concentration and thus influences the emitted visible light color. The doping concentration can adjust the color from about (0.16, 0.34) to about (0.32, 0.51) in CIE chromaticity coordinates.

Accordingly, the present invention has the following advantages:

(1) The organic light-emitting material uses five-five member rings to be the ligands of a transition metal complex. Because the conjugate ring of the ligands of the organic light-emitting material is smaller than that of a traditional organic light-emitting material, the light-emitting wavelength of the organic light-emitting material is more blue shift than that of the traditional light-emitting material.

(2) The organic light-emitting material has broader adjustable wavelength range than that of a traditional light-emitting material. The light-emitting color can be altered by changing substituents of the five-five member rings of the ligands of the transition metal complex of the organic light-emitting material.

(3) The organic light-emitting material can provide the three colors of red, blue and green, which are needed by the traditional full color displays and white light organic light-emitting devices. Moreover, the light-emitting quality of the organic light-emitting material is good and the luminescence efficiency of the organic light-emitting material is high.

(4) The luminescence efficiency of the organic light-emitting device is about 4 cd/A to about 10 cd/A.

The preferred embodiments of the present invention described above should not be regarded as limitations to the present invention. It will be apparent to those skilled in the art that various modifications and variations can be made to the present invention without departing from the scope or spirit of the invention. The scope of the present invention is as defined in the appended claims.

What is claimed is:

1. An organic light-emitting material having the structure of Formulas I or II,

Formula I

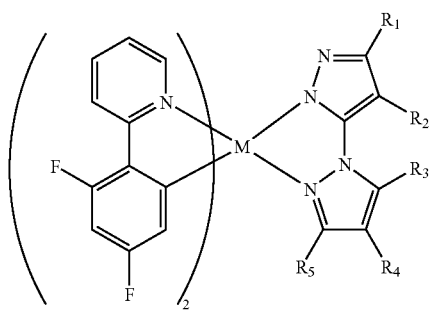

Formula II

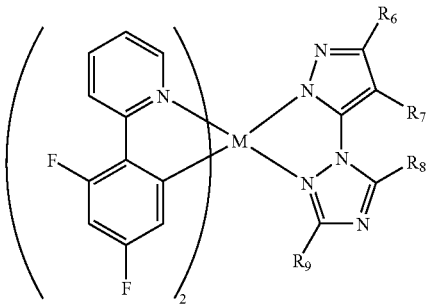

wherein each of $R_1$-$R_9$ is independently H, F, $CF_3$, an alkyl group of 1 to 6 carbon atoms, or an aryl group; and M is a transition metal atom.

2. The organic light-emitting material of claim 1, wherein the transition metal atom is Ir, Ru, Rh, Pd, Os or Pt.

3. The organic light-emitting material of claim 1, wherein the transition metal atom is Ir.

4. The organic light-emitting material of claim 1, wherein the organic light-emitting material emits phosphorescence in a wavelength range of about 450 nm to about 550 nm.

5. A method for manufacturing the organic light-emitting material of claim 1, comprising reacting a compound of Formula III with a compound of Formula IV or a compound of Formula V, and with a base compound in a solvent, Formula III

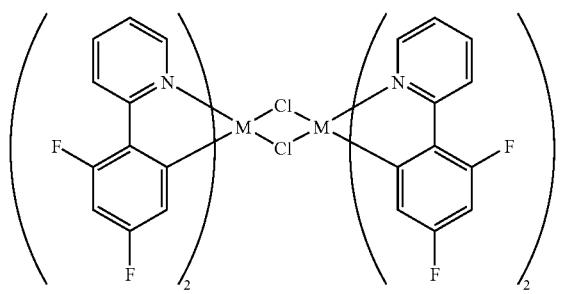

Formula IV

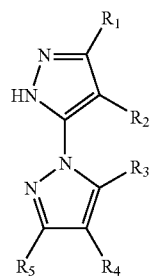

Formula V

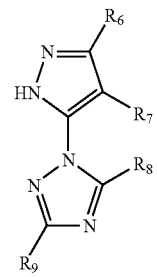

wherein each of $R_1$-$R_9$ is independently H, F, $CF_3$, an alkyl group of 1 to 6 carbon atoms, or an aryl group; and M is a transition metal atom.

6. The method of claim 5, wherein the transition metal atom is Ir, Ru, Rh, Pd, Os or Pt.

7. The method of claim 5, wherein the transition metal atom is Ir.

8. The method of claim 5, wherein the base compound is sodium ethoxide, potassium hydroxide, or sodium hydroxide.

9. The method of claim 5, wherein the solvent is ethylene glycol monoethyl ether.

10. The method of claim 5, wherein the reaction is reacted under a thermal reflux environment.

11. An organic light emitting device, which comprises:
an anode;
a cathode; and
a light-emitting layer therebetween, wherein the light-emitting layer contains an organic light-emitting material having the structure of Formulas I or II, Formula I

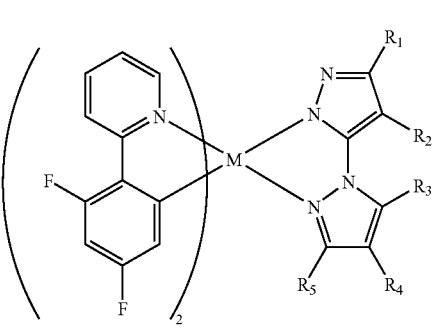

-continued

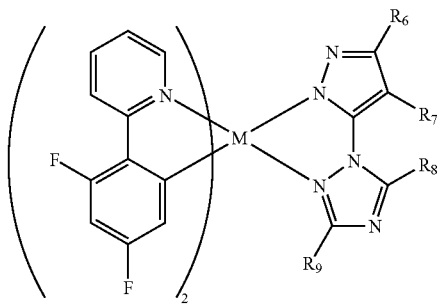

Formula II wherein each of $R_1$-$R_9$ is independently H, F, $CF_3$, an alkyl group of 1 to 6 carbon atoms, or an aryl group; and M is a transition metal atom.

12. The organic light-emitting device of claim 11, wherein the transition metal atom is Ir, Ru, Rh, Pd, Os or Pt.

13. The organic light-emitting device of claim 11, wherein the transition metal atom is Ir.

14. The organic light-emitting device of claim 11, wherein the organic light emitting device emits phosphorescence in a wavelength range of about 450 nm to about 550 nm.

15. The organic light-emitting device of claim 11, further comprising a hole injecting layer, a hole transporting layer, and an electron transporting layer, wherein these layers are oriented in the order of the anode, the hole injecting layer, the hole transporting layer, the light-emitting layer, the electron transporting layer and the cathode.

* * * * *